US012127890B1

(12) United States Patent
Gorrepati

(10) Patent No.: US 12,127,890 B1
(45) Date of Patent: Oct. 29, 2024

(54) MIXED REALITY ENDOSCOPIC RETROGRADE CHOLANGIOPANCREATOPGRAPHY (ERCP) PROCEDURE

(71) Applicant: Navakanth Gorrepati, Southlake, TX (US)

(72) Inventor: Navakanth Gorrepati, Southlake, TX (US)

( * ) Notice: Subject to any disclaimer, the term of this patent is extended or adjusted under 35 U.S.C. 154(b) by 277 days.

(21) Appl. No.: 17/399,586

(22) Filed: Aug. 11, 2021

(51) Int. Cl.
*A61B 90/00* (2016.01)
*A61B 1/273* (2006.01)

(52) U.S. Cl.
CPC ............... *A61B 90/37* (2016.02); *A61B 1/273* (2013.01); *A61B 2090/365* (2016.02)

(58) Field of Classification Search
CPC ....... A61B 8/468; A61B 6/4417; A61B 6/468; A61B 6/5235; A61B 8/0883; A61B 8/12; A61B 8/4209; A61B 8/4245; A61B 8/4416; A61B 8/5261; A61B 6/501; A61B 1/01; A61B 1/0004; A61B 1/0005; A61B 1/273; A61B 90/37; A61B 2090/365; G05B 15/02; G02B 27/017; G06F 3/011
See application file for complete search history.

(56) References Cited

U.S. PATENT DOCUMENTS

| 5,810,807 | A  | * | 9/1998 | Ganz ................... A61B 18/1492 606/113 |
| 6,346,940 | B1 | * | 2/2002 | Fukunaga ............... G06T 15/20 382/103 |
| 10,220,181 | B2 |  | 3/2019 | Giap et al. |
| 2001/0027272 | A1 | * | 10/2001 | Saito .................... A61B 1/0005 600/429 |
| 2005/0033117 | A1 | * | 2/2005 | Ozaki .................... G16H 40/63 600/117 |
| 2008/0243142 | A1 | * | 10/2008 | Gildenberg ............ G16H 30/40 606/130 |
| 2009/0012390 | A1 | * | 1/2009 | Pescatore .............. G06T 7/0012 600/425 |
| 2010/0057077 | A1 | * | 3/2010 | Ducharme ............. A61B 18/14 606/39 |

(Continued)

FOREIGN PATENT DOCUMENTS

WO WO2016/028828 A1 2/2016

OTHER PUBLICATIONS

Liu et al., "Monitoring with Head-Mounted Displays: Performance and Safety in a Full-Scale Simulator and Part-Task Trainer", Oct. 2009 (Year: 2009).*

(Continued)

*Primary Examiner* — Adil Partap S Virk
(74) *Attorney, Agent, or Firm* — Law Office of Sam Sokhansanj PLLC

(57) ABSTRACT

A mixed reality endoscopic surgical procedure method, including the steps of selecting a holographic first image of a body part to be surgically operated on in three-dimensional form and displaying the holographic first image of the body part. The method can further include positioning an endoscope relative to the body part, wherein the endoscope further includes a guidewire, displaying a second holographic image or video of the endoscope or guidewire relative to the body part, and using the first holographic first image as a visual guide for engaging the body part via the guidewire.

4 Claims, 12 Drawing Sheets

(56) References Cited

U.S. PATENT DOCUMENTS

| | | | |
|---|---|---|---|
| 2013/0211246 A1 | 8/2013 | Parasher | |
| 2014/0303491 A1* | 10/2014 | Shekhar | G06T 7/337 |
| | | | 600/424 |
| 2015/0123946 A1* | 5/2015 | Kawamura | G09G 5/10 |
| | | | 345/175 |
| 2015/0126859 A1* | 5/2015 | Popovic | A61B 6/504 |
| | | | 600/426 |
| 2015/0141808 A1* | 5/2015 | Elhawary | A61B 5/7264 |
| | | | 600/424 |
| 2016/0216515 A1* | 7/2016 | Bouchier | G06T 19/006 |
| 2017/0007350 A1* | 1/2017 | Popovic | A61B 34/10 |
| 2017/0202633 A1* | 7/2017 | Liu | G16H 20/40 |
| 2017/0357332 A1 | 12/2017 | Balan et al. | |
| 2018/0116714 A1* | 5/2018 | Karpiel | A61B 18/1492 |
| 2019/0290247 A1* | 9/2019 | Popovic | A61B 1/0005 |
| 2019/0374279 A1* | 12/2019 | Weitzner | A61B 90/39 |
| 2020/0179039 A1* | 6/2020 | Yanuma | A61B 18/1492 |
| 2021/0100528 A1* | 4/2021 | Dayton | A61B 1/0051 |
| 2021/0137350 A1* | 5/2021 | Inglis | A61B 34/10 |
| 2021/0169330 A1* | 6/2021 | Komp | A61B 5/062 |
| 2022/0104896 A1* | 4/2022 | Shelton, IV | G06F 3/147 |
| 2022/0110504 A1* | 4/2022 | Inglis | A61B 90/37 |

OTHER PUBLICATIONS

Katsinelos et al., "Comparison of Three Types of Precut Technique to Achieve Common Bile Duct Cannulation: A Retrospective Analysis of 274 Cases", Jun. 20, 2012 (Year: 2012).*

Nguyen et al., "Markerless Tracking for Augmented Reality for Image-Guided Endoscopic Retrograde Cholangiopancreatography", Jul. 2013 (Year: 2013).*

Shimatani et al., "Tips for double balloon enteroscopy in patients with Roux-en-Y reconstruction and modified Child surgery", Dec. 2013 (Year: 2013).*

Pöhlmann et al., "Evaluation of Kinect 3D Sensor for Healthcare Imaging", J. Med. Biol. Eng. (2016) 36:857-870; 14 pp. total.

Jerbi et al., "Anatomical and morphometric study of gastrointestinal tract of donkey (*Equus africanus* asinus)", J. Morphol. Sci., 2014, vol. 31, No. 1, p. 18-22; 5 pp. total.

Edmundowicz, Steven A, "Wire Guided Cannulation: Clinical Perspective, a Review of the Literature and Appraisal of the Technique", Mar. 2013; 4 pp. total.

* cited by examiner

MIXED REALITY ENDOSCOPIC RETROGRADE CHOLANGIOPANCREATOPGRAPHY (ERCP) PROCEDURE

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

Endoscopic retrograde cholangiopancreatography (ERCP) is an endoscopic surgical procedure that involves placement of a viewing instrument, such as an endoscope or a duodenoscope, within the duodenum of a patient. ERCP is an alternative to invasive surgery for the identification and/or treatment of obstructions and abnormalities of the biliary and pancreatic ducts. It is possible to pass additional medical devices through the endoscope for treatment and diagnostic purposes, such as a catheter, or for navigational purposes, such as a guide wire. Generally, a physician can perform an ERCP by inserting and guiding an endoscope through a patient's alimentary canal-esophagus, stomach, and duodenum. The physician can stop advancing the endoscope upon reaching the area of the duodenum where the ducts of the biliary tree and the pancreas open into the duodenum. This opening or orifice is commonly referred to the major duodenal papilla or major papilla (MP), ampulla of Vater, or papilla of Vater, and is a small mound of tissue which can resemble a nipple in appearance.

After guiding the endoscope to the major papilla, sphincterotome or a catheter, for example a biliary catheter, can be inserted through the endoscope so that the distal end of the biliary catheter emerges from the distal end of the endoscope. Cannulation is the passage of a guidewire, catheter, or other devices through a duodenoscope into the bile duct or pancreatic duct at ERCP. The biliary catheter can be used for cannulation of the major papilla orifice in order to access additional anatomical structures, for example, the intraduodenal portion of the bile duct, the intrapancreatic portion of the common bile duct, and the common bile duct, among others. Cannulation of the major papilla can be achieved by probing the duodenum and ampulla tissue with the tip of the sphincterotome, endoscope and, if necessary, a guide wire. However, despite best efforts, a physician can be unsuccessful in cannulation. Additionally, excessive probing of the tissue can lead to inflammation and patient discomfort. Further, forceful probing of the major papilla region could cause ampullary trauma or pancreatic duct damage, or other potential life threatening injuries. Although an endoscope can be equipped with a visualization apparatus, for example a direct light visualization apparatus, this does not eliminate or greatly reduce the difficulty in cannulation of the major papilla. Moreover, the fact that many ERCP procedures, in particular cannulation of the major papilla, are performed by a single physician without additional real time support or guidance from other colleagues or physicians, further contribute to unsuccessful or prolonged cannulation of the major papilla.

Further, mixed reality is a technology that allows virtual imagery to be mixed with a real-world physical environment in a display. Systems for mixed reality may include, for example, see through head mounted display (HMD) devices or smart phones with built in cameras. Such systems typically include processing units which provide the imagery under the control of one or more applications. Full virtual reality environments in which no real-world objects are viewable can also be supported using HMD and other devices. Such systems may also include one or more wireless hand-held inertial controllers that the user of the system can manipulate to interact with the HMD and provide user input to the HMD, including, but not limited to, controlling and moving a virtual cursor, selection, movement and rotation of objects, scrolling, etc. However, there is currently no such mixed reality or HMD device that includes programming to assist a physician in ERCP procedures, and in particular, cannulation of the major papilla.

Hence, what is needed is an effective and efficient guiding method and system using a mixed reality or HMD device that allows a physician better control in the cannulation of the major papilla during ERCP, thereby minimizing or eliminating excessive probing of the major papilla tissue region and further preventing inflammation, ampullary trauma, and/or pancreatic duct damage, among others. In addition, what is needed is a system that provides readily available visualizations of imaging studies of the abdomen such as a CT scan, MRCP, and MRI (such as coronal views) in cases of difficult biliary access in real time to help in advancing the direction of the catheter towards the common bile duct or the pancreatic duct. In addition, what is further needed is a system that allows multiple physicians performing such an ERCP procedure to collaborate with each other in real-time to not only provide instructional information but to further assist the performing physician in successful cannulation of the major papilla.

BRIEF SUMMARY

In one aspect of the disclosure described herein, an effective and efficient guiding method and system is disclosed using a mixed reality or head mounted device that allows a physician better control in the cannulation of the major papilla during an ERCP procedure, thereby minimizing or eliminating excessive probing of the major papilla tissue region and further preventing inflammation, ampullary trauma, and/or pancreatic duct damage, among others. The mixed reality device can include readily available visualizations of imaging studies of the abdomen such as a CT scan, MRCP, and MRI (such as coronal views) in cases of difficult biliary access in real time which also helps in advancing the direction of the catheter towards the common bile duct or the pancreatic duct. In addition, the system of the disclosure described herein can allow multiple physicians performing such an ERCP procedure to collaborate with each other in real-time to not only provide instructional information but to further assist the performing physician in successful cannulation of the major papilla.

In another aspect of the disclosure described herein, a mixed reality ERCP (hereinafter "MR-ERCP") or mixed reality endoscopic surgical procedure method is disclosed comprising the steps of selecting a holographic first image of a body part to be surgically operated on in three-dimensional form, displaying the holographic first image of the body part. The method further includes positioning an endoscope relative to the body part, wherein the endoscope further comprises a guidewire, displaying a second holographic image or video of the endoscope or guidewire relative to the body part, and using the first holographic first image as a visual guide for engaging the body part via the guidewire.

Further, the first holographic first image being a duodenum illustrating a major papilla orifice or ampulla. In addition, the body part can be the major papilla orifice or ampulla. In addition, the second holographic image or video can be at least one of: a fluoroscopic x-ray, endoscopic camera view, or a magnetic resonance cholangiopancreatography (MRCP) or a 3D reconstructed MRCP/CT of the major papilla. Here, the endoscope can include a sphincterotome. Further, the step of positioning can further include orientating the sphincterotome in an about 10 to 11 o'clock position relative to the position of the first holographic image of the body part. Alternatively, the step of positioning can further include orientating the sphincterotome in an about 30-degree to about 60-degree position relative to a horizontal plane and further with respect to the position of the first holographic image of the body part.

The mixed reality endoscopic surgical procedure method can further include displaying a third holographic image or video relative to the first holographic image and second holographic image or video. In addition, the method can also include displaying one or more holographic information of patient vitals. Here, the second holographic image or video can further include streaming one or more video or image data from a first source. The method can further include displaying one or more holographic images of one or more users and further communicating with the one or more users via audio or video.

In another aspect of the disclosure described herein, a mixed reality endoscopic surgical procedure method is disclosed. The method can include selecting a holographic first image of a body part to be surgically operated on in three-dimensional form, displaying the holographic first image of the body part, and positioning an endoscope relative to the body part, wherein the endoscope further comprises a guidewire. The method can further include displaying a second holographic image or video of the endoscope or guidewire relative to the body part, and using the first holographic first image as a visual guide for engaging the body part via the guidewire. In addition, the first holographic first image can include a duodenum illustrating a major papilla orifice or ampulla. Further, the body part can include the major papilla orifice or ampulla. In addition, the second holographic image or video can include at least one of: a fluoroscopic x-ray, endoscopic camera view, a magnetic resonance cholangiopancreatography (MRCP), or a 3D reconstructed MRCP/CT scan. Further, the endoscope can further a sphincterotome.

The method can also include wherein the step of positioning further includes orientating the sphincterotome in an about 10 to 11 o'clock position relative to the position of the first holographic image of the body part. In addition, the step of positioning can further include orientating the sphincterotome within a range of about 10-degrees to about 80-degrees relative to a horizontal plane and further with respect to the position of the first holographic image of the body part. The method can also include displaying a third holographic image or video relative to the first holographic image and second holographic image or video. In addition, the method can include displaying one or more holographic information of patient vitals. Here, the second holographic image or video is can further include streaming one or more video or image data from a first source. The method can further include displaying one or more holographic images of one or more users and further communicating with the one or more users via audio or video.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

Figure 1:
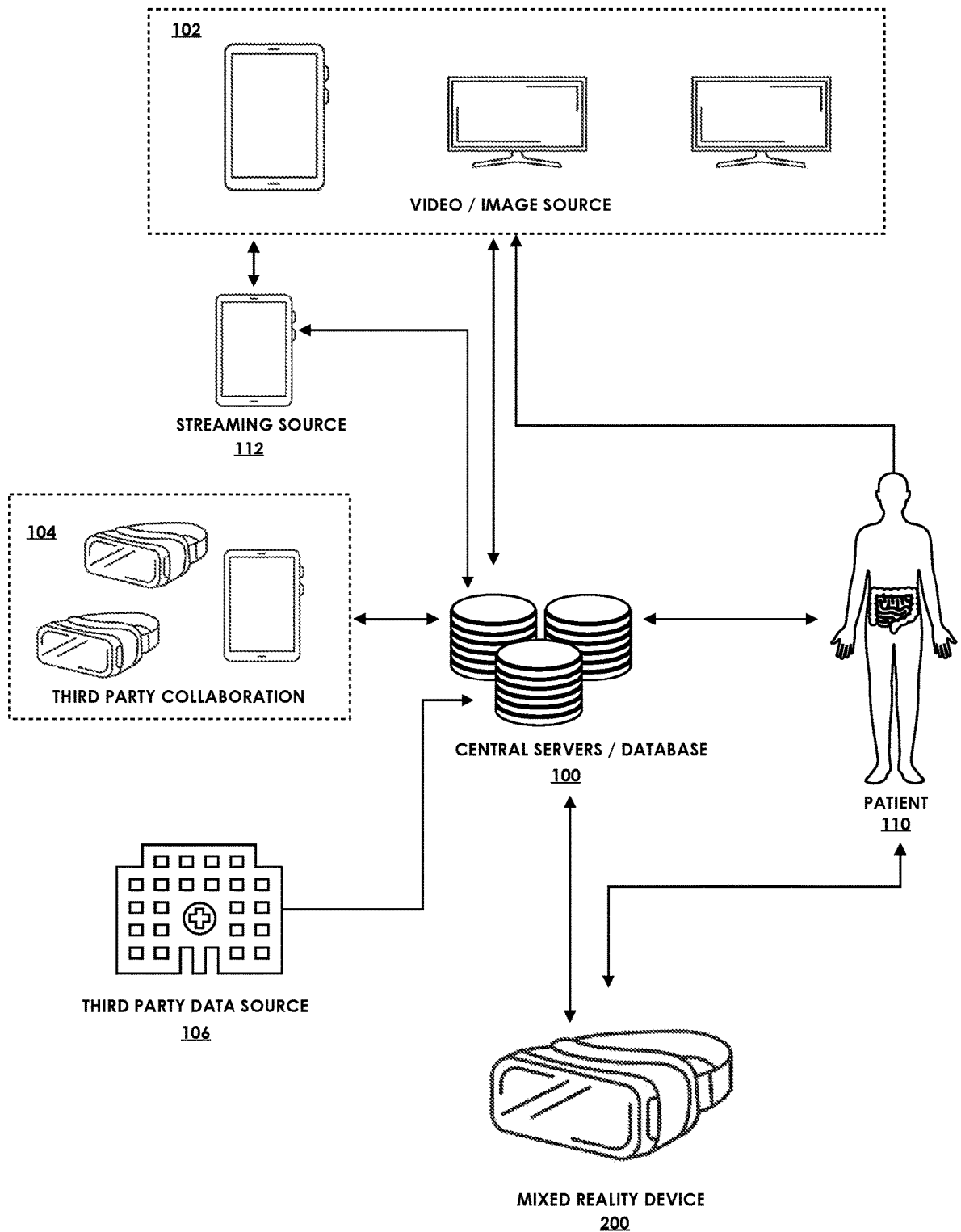
FIG. 1 illustrates an overview block diagram for one non-limiting exemplary embodiment of a network architecture of the augmented or mixed reality ERCP (MR-ERCP) apparatus, system, and method of the disclosure described herein.

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

In one implementation of the disclosure described herein, a display page may include information residing in the computing device's memory, which may be transmitted from the computing device over a network to a central database center and vice versa. The information may be stored in memory at each of the computing device, a data storage resided at the edge of the network, or on the servers at the central database centers. A computing device or mobile device may receive non-transitory computer readable media, which may contain instructions, logic, data, or code that may be stored in persistent or temporary memory of the mobile device, or may somehow affect or initiate action by a mobile device. Similarly, one or more servers may communicate with one or more mobile devices across a network and may transmit computer files residing in memory. The network, for example, can include the Internet, wireless communication network, or any other network for connecting one or more mobile devices to one or more servers.

Any discussion of a computing, mobile device, head mounted display (HMD) may also apply to any type of networked device, including but not limited to mobile devices and phones such as cellular phones (e.g., an iPhone®, Android®, Blackberry®, or any "smart phone"), a personal computer, iPad®, server computer, or laptop computer; personal digital assistants (PDAs); augmented reality head mounted display, virtual reality head mounted display, mixed reality head mounted display, or Microsoft® HoloLens 1, 2, Magic Leap, or any future iteration thereof a roaming device, such as a network-connected roaming device; a wireless device such as a wireless email device or other device capable of communicating wireless with a computer network; or any other type of network device that may communicate over a network and handle electronic transactions. Any discussion of any mobile or computing device mentioned may also apply to other devices, such as devices including Bluetooth®, near-field communication (NFC), infrared (IR), and Wi-Fi functionality, among others.

Phrases and terms similar to "software", "application", "app", and "firmware" may include any non-transitory computer readable medium storing thereon a program, which when executed by a computer or computing device, causes the computer or computing device to perform a method, function, or control operation.

Phrases and terms similar "network" may include one or more data links that enable the transport of electronic data between computer systems and/or modules. When information is transferred or provided over a network or another communications connection (either hardwired, wireless, or a combination of hardwired or wireless) to a computer, the computer uses that connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Phrases and terms similar to "portal" or "terminal" may include an intranet page, internet page, locally residing software or application, mobile device graphical user interface, holographic projected screen, holographic projection, holographic visualization, free space display, two-dimensional or three-dimensional object projection, head mounted display (HMD) or visual graphical presentation, or digital presentation for a user. The portal may also be any graphical user interface for accessing various modules, features, options, and/or attributes of the disclosure described herein. For example, the portal can be a web page accessed with a web browser, mobile device application, any application or software residing on a computing device, or any image, graphic, sound, or video presented on a computing device.

FIG. 1 illustrates one non-limiting exemplary embodiment of a network architecture of the mixed reality endoscopic retrograde cholangiopancreatography (MR-ERCP) of the disclosure described herein. In particular, the MR-ERCP system can include one or more mixed reality devices 200 that can communicate bi-directionally with central servers or databases 100. Here, such communication may be before, during, or after an ERCP procedure of a patient 110. Here, device 200 is configured to be used in conjunction with the process of inserting an endoscope and sphincterotome through the patient's esophagus, stomach, duodenum, and major papilla, and further for retrieving the endoscope and sphincterotome. The MR-ERCP system may also include various image and video sources 102 for obtaining, retrieving, distributing, transmitting, and streaming any type of images, video, digital renderings, or visual representations information of various regions or areas of patient 100, including areas associated with the gastro intestinal regions, including but not limited to the esophagus, stomach, large intestines, small intestines, pancreas, gall bladder, duodenum, major papilla, minor papilla, biliary tree, common bile duct, and pancreatic duct, among others. In particular, such information from video source 102 may be obtained in real-time during an ERCP, such as live video feed from an endoscopic camera inserted in the patient and, three-dimensional MRCP/CT reconstruction, including any x-ray fluoroscopy contrast images obtained or renderings, among others.

Still referring to FIG. 1, mixed reality device 200 can be any type of head mounted display (HMD), such as a mixed reality headset, augmented reality headset, or virtual reality headset having a visual display or visual presentation of objects in space. In addition, device 200 may also include one or more optical sensors for detecting the presence of a user's hand within a field of view of the optical sensor, determining by the optical sensor of the HMD of device 200 the location and orientation of the user's (or the physician's) hand relative to the HMD which allows the user or physician to control and move a virtual cursor, a selection, and one or more objects, and further scroll through other visual graphics such as photos, videos, or documents. In addition, the optical sensor may also continuously track the movement of the user's hand relative to the HMD over a period of time. Further, the HMD of device 200 may also include a depth and/or time-of-flight camera that is capable of detecting three-dimensional location of objects located within the depth camera's field of vision. In particular, the HMD allows for object visualization in three-dimension over real word physical objects in an environment as holograms or holographic images. These holograms can be placed in space in the field of view of the user of the HMD next to other image or video sources, such as an endoscopy and x-ray monitor or video feed. In addition, the HMD of device 200 may provide six degrees of freedom, where the user can move images or objects in space (such as holographic images) in a forward, backward, up, down, right, left, pitch, yaw and roll configuration or orientations. In addition, device 200 may also include artificial intelligence (AI) or machine learning algorithms for learning patterns and history of the user's hand relative to the HMD to anticipate or predict future actions with accuracy. Such learning may include prior usage of various patient information and previously used images and video pertaining to an ERCP procedure. In addition, device 200 may also include the ability to respond to various voice commands from the user or physician, which can include but are not limited to, retrieving various images or video for display to the physician during an ERCP.

Still referring to FIG. 1, the MR-ERCP system may also include various third-party collaboration computing device sources 104. In particular, a user or physician using mixed reality device 200 may be able to collaborate, communicate, or share his or her mixed reality device's HMD screen with other physicians or other users via sources 104. In particular, the user of device 200 may be able to share the visual representation of the display on his or her HMD with one or more users via sources 104. This may include sharing real-time streaming video and image feeds from an ERCP procedure, such as a three-dimensional view of the duodenum and major papilla, endoscopic camera view, 3d magnetic resonance cholangiopancreatography (MRCP) and fluoroscopic x-ray views. Here, the MR-ERCP system of the disclosure described herein may include its own independent application or software residing on streaming computing device source 112 independent of the device 200, such that the application allows for the aforementioned image and video from various sources (such as the endoscopic camera/image/video, MRCP camera/image/video, and fluoroscopic x-ray camera/image/video) to be streamed in real-time via the ERCP network to the HMD or portal of one of more devices 200. In particular, the MR-ERCP system of the disclosure described may have its own application programming interface (API) for allowing software on source 112 to communicate with the software of device 200. In addition, various other users or collaborators may also share any type of data, information, videos, and/or images to the display of device 200 either before, during, and after an ERCP procedure, including voice and video communication with various parties. In addition, the MR-ERCP system may also communicate bidirectionally with various third-party sources 106. Here, third party sources 106 may include patient related information being retrieved or transmitted to other physicians, clinics, operating rooms, insurance providers, and hospitals in a secure HIPPA compliant environment. In addition, sources 106 may also be able to transmit various information about a patient in real-time to the HMD of device 200 via central servers 100.

Figure 2:
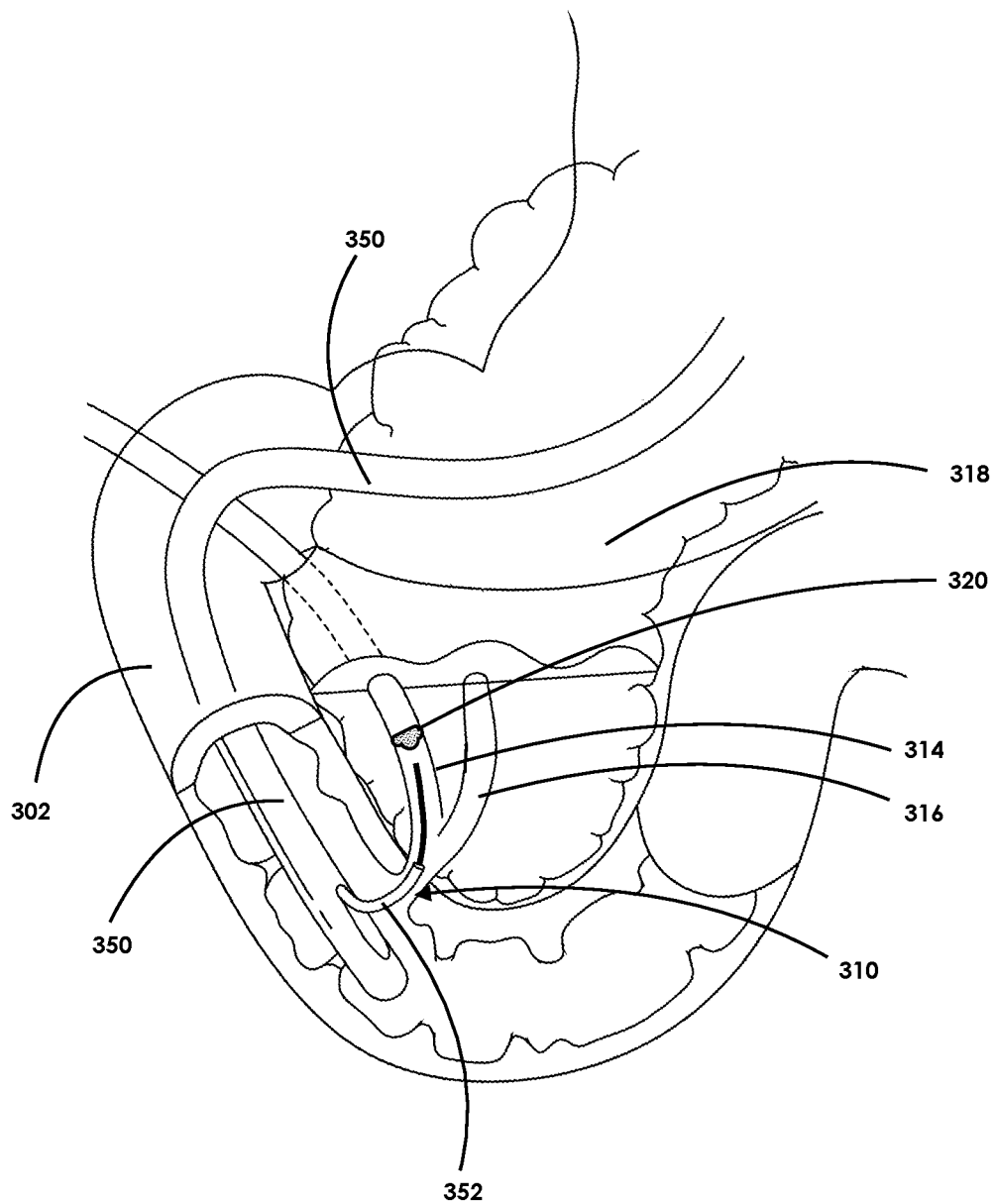
FIG. 2 illustrates a simplified partial cross-sectional view diagram of an ERCP procedure with respect to cannulation of a major papilla of the duodenum.
Figure 11:
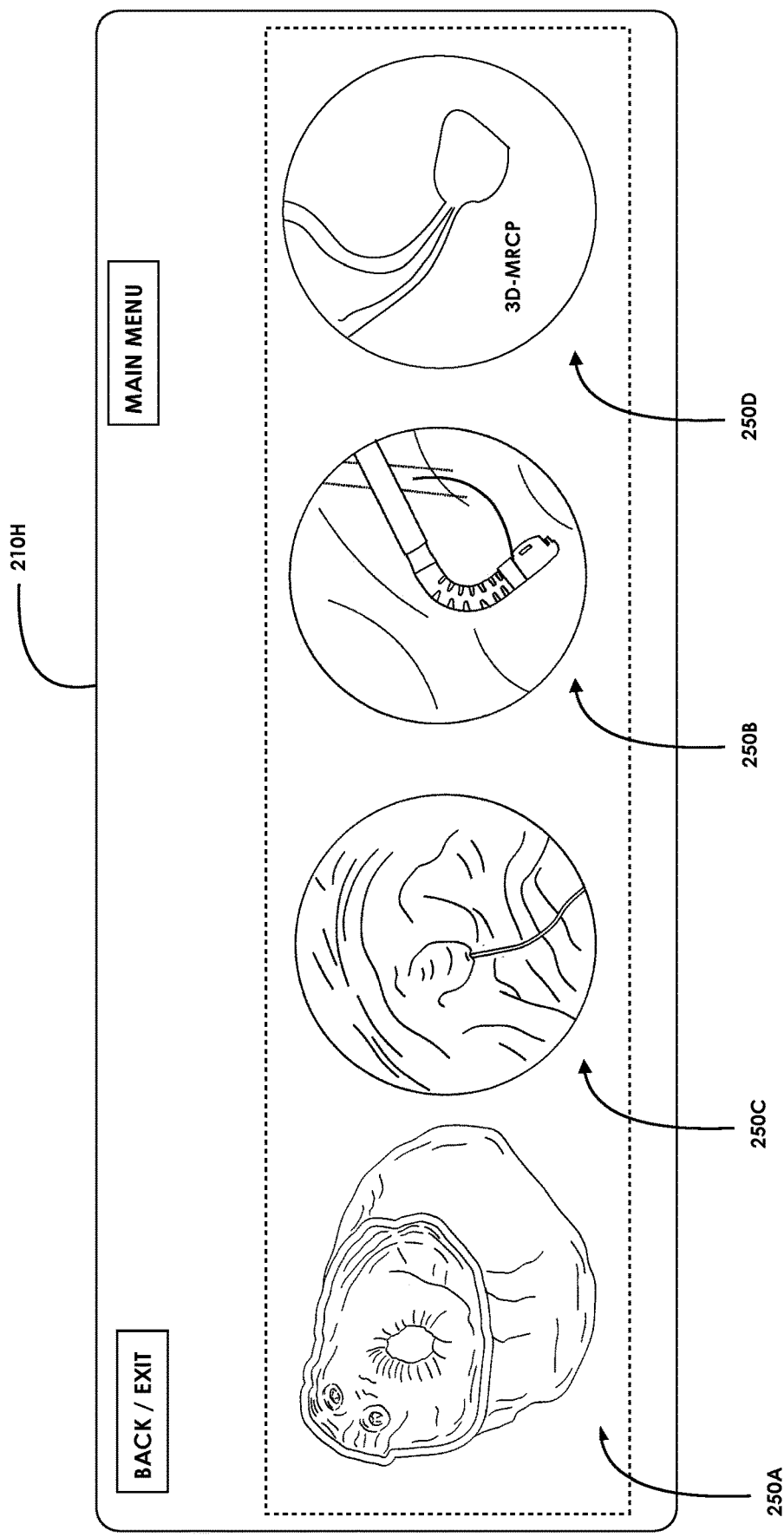
FIG. 11 illustrates another graphical screen, projection, or holographic visualization portal of the MR-ERCP system, method, and apparatus of the disclosure described herein, depicting various three-dimensional, endoscopic, x-ray views, and 3D MRCP holographic images in relation to each other during an ERCP procedure of the patient in real-time.

FIG. 2 illustrates one non-limiting exemplary embodiment of an ERCP procedure method using the MR-ERCP of the disclosure described herein, illustrating a simplified gastrointestinal area of a patient. In particular, the surgeon, physician, endoscopist, or user may begin by initiating the HMD of device 200 to display the endoscopic camera video feed in real time from endoscope 350 as the endoscope is being inserted through a patient's esophagus, to the stomach, and subsequently to the duodenum region 302. Here, the endoscope 350 can include a sphincterotome having a catheter or guidewire 352 that is configured to extend in a curved orientation to penetrate the major papilla orifice 310. Here, as will be discussed later in detail, the display on the HMD of device 200 would provide the user realistic perception of the orientation and location of the major papilla orifice 310 in a three-dimensional space to provide successful cannulation of orifice 310. Specifically, the three-dimensional reconstructed MRCP/CT abdomen views of the cranial part of the duodenum (such as shown in FIG. 11) or holographic image of the cranial part of the duodenum (such as shown in FIGS. 3A-3B) can guide the physician to bend the guidewire of the sphincterotome at the right angle, curvature, direction, and orientation in order to successfully penetrate the major papilla orifice 310.

Still referring to FIG. 2, once the catheter or guidewire 352 is inserted within orifice 310, it can be further guided to the appropriate duct, such as the common bile duct 314 or the pancreatic duct 316 that connects to the pancreas 318. In one example, once successful cannulation has been achieved within the common bile duct 314, the user may further operate and manipulate the guidewire 352 to free or open duct 314 from any type of obstructing object 320, such as gallstones or bile duct stones. While not shown in FIG. 2, the MR-ERCP method may also be used for cannulation of the minor papilla orifice. In addition, the MR-ERCP of the disclosure described herein may also be used for assisting the surgeon in guiding guidewire 352 into the pancreatic duct 316. It is contemplated within the scope of the present disclosure described herein that the HMD of device 200 may modify or change different images, orientations, and videos in real-time depending on the stage of the ERCP procedure, either automatically or as initiated by the user or surgeon.

Figure 3A:
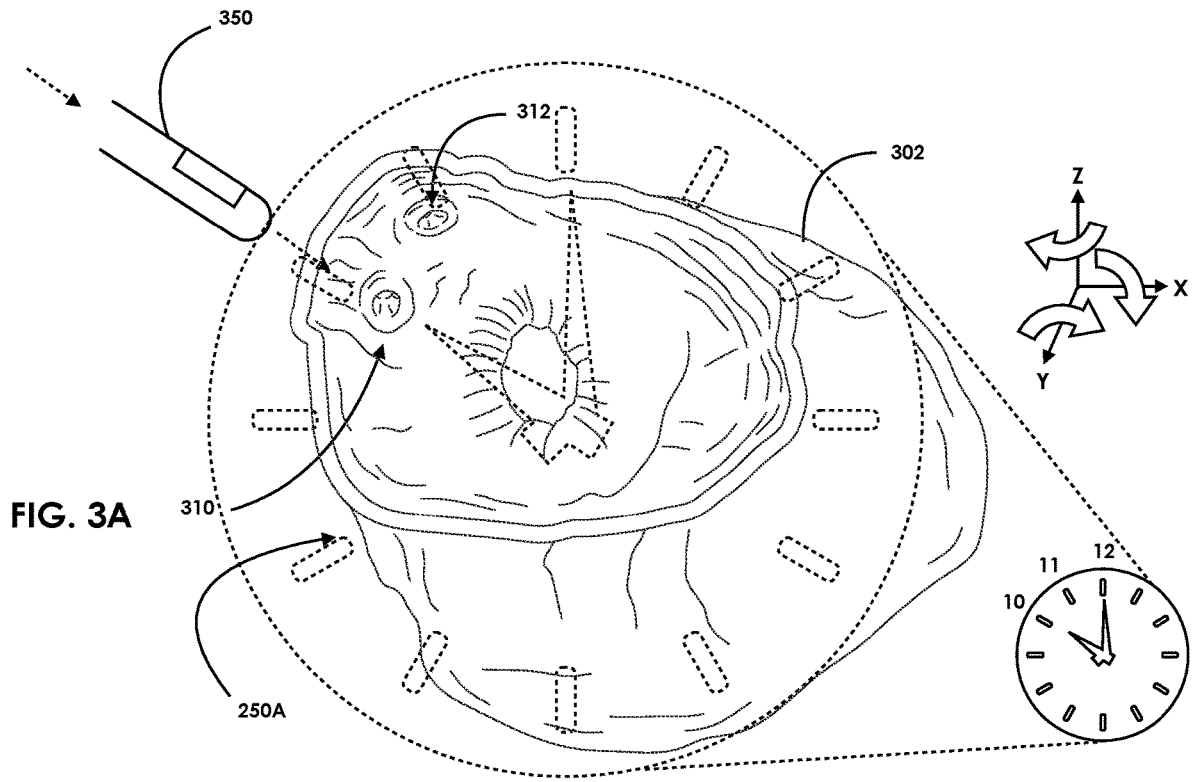
FIG. 3A illustrates a perspective view of a rotatable three-dimensional view of a cranial part of the duodenum used with the MR-ERCP of the disclosure described herein.

FIG. 3A illustrates one non-limiting exemplary embodiment of a three-dimensional holographic image 250A of the ampulla 310 that is to be displayed on the HMD or portal of device 200, wherein the anatomy of the duodenum 302 depicts the ampulla or major papilla orifice 310. For illustrative purposes, a holographic image of a clock can be projected and superimposed to illustrate the position of the sphincterotome relative to ampulla 310 or 312 of image 250A, further depicting the hour hand. The sphincterotome, which has been pre-loaded with a guidewire, is directed to the biliary orifice at an about a 10 o'clock or between a 10-11 o'clock position (or between about a 10 to 80 degree angle relative to a vertical plane or y-axis, or between about a 100 to 170 degree angle relative to a horizontal plane or x-axis, to, or between about a 10 to 80 degree angle from a vertical plane or from the 12 o'clock hour hand) towards and adjacent to the ampulla wherein cannulation is attempted between the 10 o'clock position 310 spaced apart at a distance from the 11 o'clock position depicted by 312. Here, it is contemplated within the scope of the present disclosure described herein that the biliary orifice in the major papilla may also be located at position 312, depending on the anatomy of the patient.

Figure 3B:
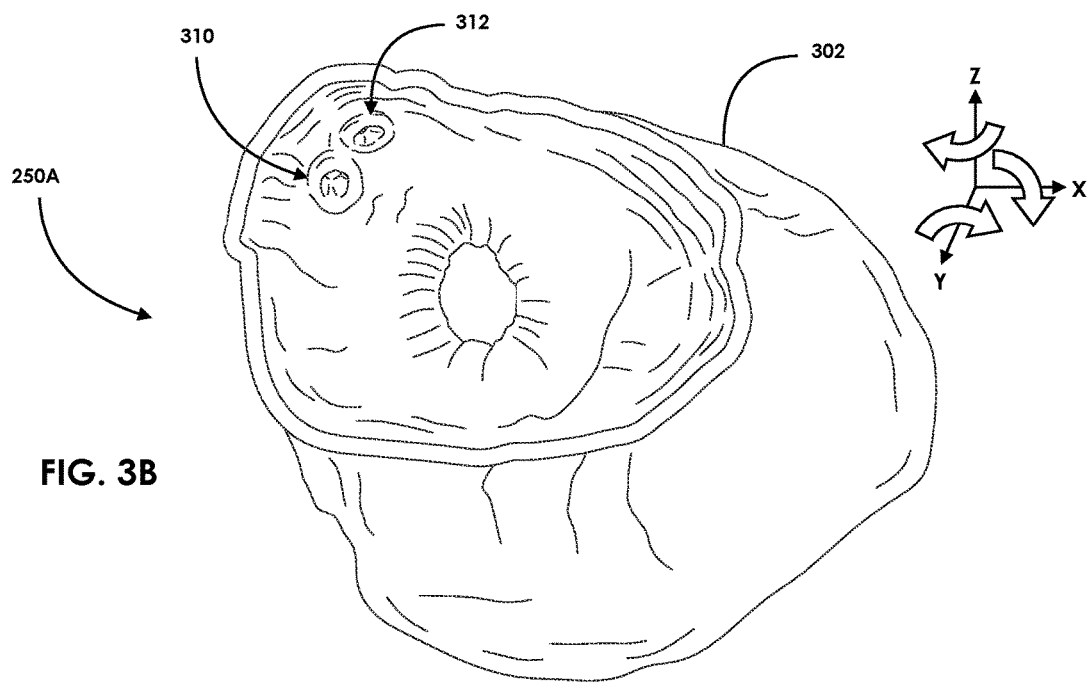
FIG. 3B illustrates another perspective view of a rotatable three-dimensional view of the cranial part of the duodenum used with the MR-ERCP of the disclosure described herein.

FIG. 3B illustrates another non-limiting exemplary embodiment of a three-dimensional holographic image 250A that is to be displayed on the HMD of device 200, wherein the anatomy of the duodenum 302 depicts the biliary orifice of the major papilla orifice at 10 o'clock 310 spaced at a shorter distance with respect to another alternative location of the biliary orifice of major papilla at 11 o'clock 312, relative to the holographic image 250A of FIG. 3A. Here, it is contemplated within the scope of the present disclosure described herein that any of the holographic image 250A of FIG. 3A or 3B may be used by the user of device 200 for the ERCP procedure, depending on the anatomy and characteristics of a particular patient being operated on. It is contemplated within the scope of the disclosure described herein that the user of device 200 may have the ability to manually (or automatically) select any image of an anatomy that is a close representation of the anatomy of the patient being operated on, including but not limited to the duodenum, ampulla, intestines, gallbladder, liver, pancreas, heart, lungs, or any other bodily organ. In addition, holographic images 250A are configured such that they can be manipulated, modified, rotated, transposed, cropped, colorized, de-colorized, sharpened, magnified/de-magnified, zoomed in or out as desired. In particular, holographic images 250A may be rotated in the x, y, z plane by manipulation of the user's hand relative to the HMD of device 200 into any orientation such that the orientation aligns with the near exact orientation of the actual physical duodenum and major papilla of the patient being operated on in real-time. In addition, holographic images 250A may also be resized in real time on the HMD of device 200.

Still referring to FIGS. 3A-3B, in one embodiment, once the desired orientation and size of holographic image 250A is achieved by the user relative to the patient, the user of device 200 can have the ability to "lock in", center, or calibrate holographic image 250A on the HMD of device 200. Once calibrated, as the user moves his or her head wearing the HMD in different distances and orientations, the holographic image 250A displayed to the user on the HMD also moves in correlation to the user's head movement. For example, as the user's head moves away from the patient, the holographic image 250A will correspondingly decrease in size, or, as the user moves his or her head in the right or left direction, the holographic image 250A will also move in the corresponding opposite direction or away from the user's field of view. Accordingly, the foregoing method provides a level consistency to the operating surgeon, where he or she knows where the guidewire is relative to the duodenum at all times, thereby improving the odds of successful cannulation of the major papilla. While not shown in FIGS. 3A-3B, three-dimensional reconstructed MRCP/CT abdomen views of the cranial part of the duodenum can be used to create views of the cranial part of the duodenum of individual patients like the holographic image of the cranial part of the duodenum in FIGS. 3A-3B. This allows successful and easy cannulation in case of variant patients' anatomy.

Figure 4A:
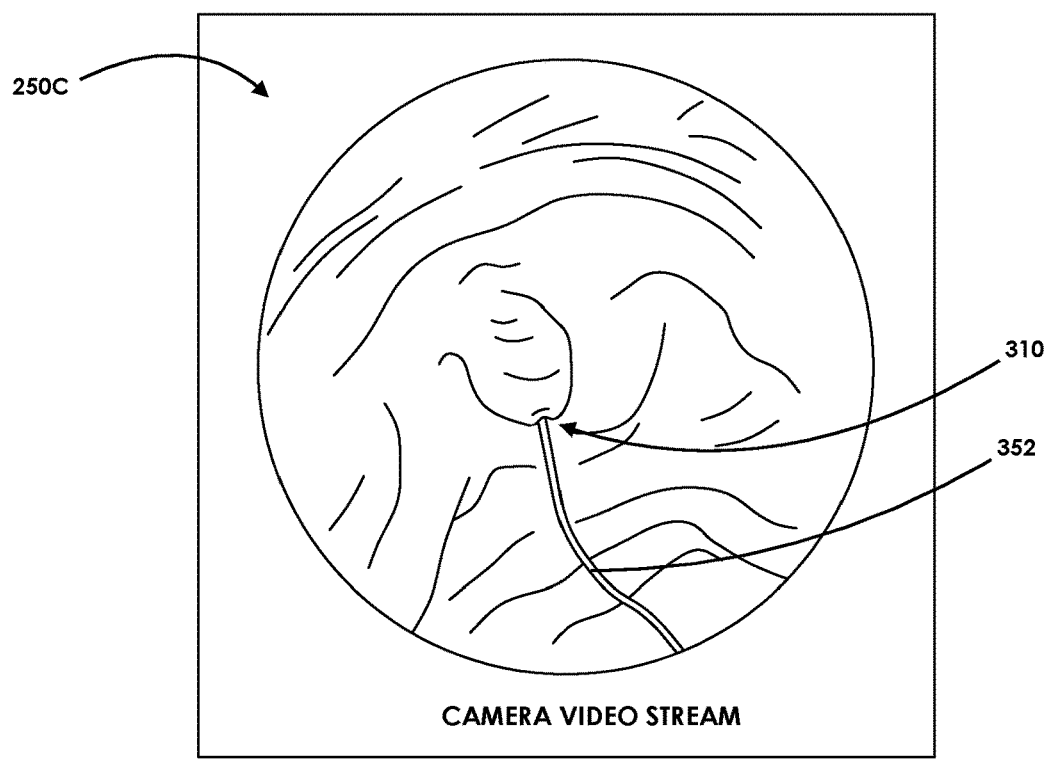
FIG. 4A illustrates a partial front camera endoscopic view of cannulation of the major papilla of the duodenum used with the MR-ERCP of the disclosure described herein.
Figure 4B:
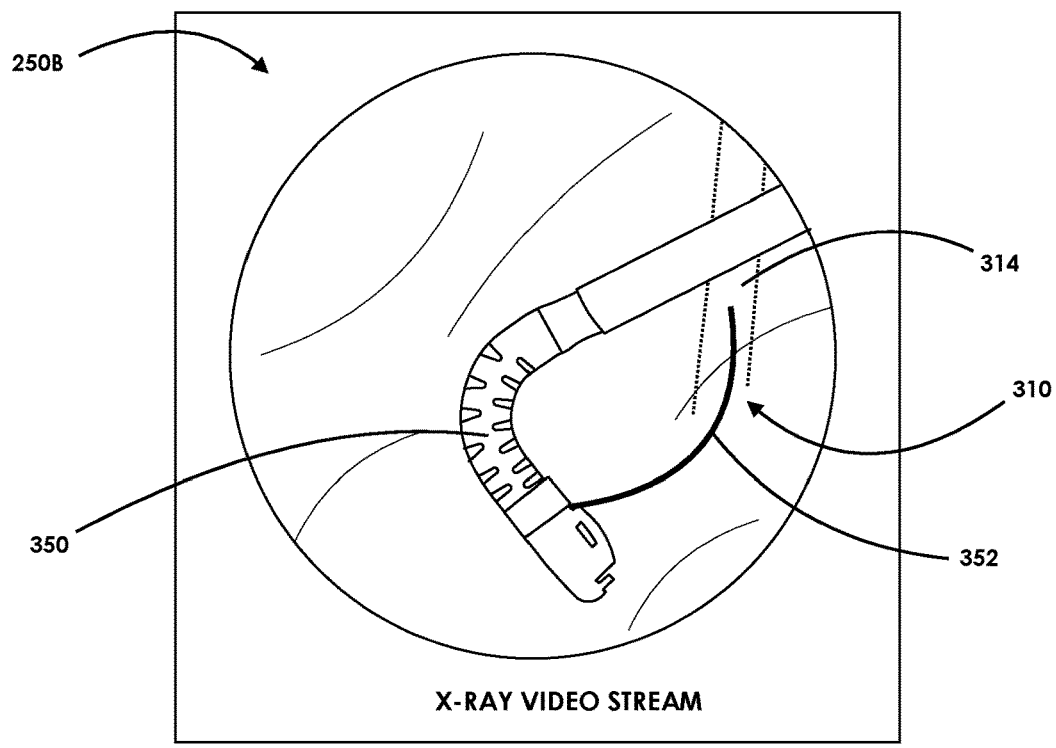
FIG. 4B illustrates a partial front fluoroscopic x-ray view of cannulation of the major papilla of the duodenum used with the MR-ERCP of the disclosure described herein.

FIG. 4A illustrates one non-limiting exemplary embodiment of the endoscopic camera image or video stream of the endoscope or sphincterotome having guidewire 352 being successfully inserted into the major papilla opening 310 and within bile duct 314. This image can be further magnified by the user to accurately identify the major papilla orifice. FIG. 4B illustrates one non-limiting exemplary embodiment of an x-ray fluoroscopy image or video stream of endoscope or sphincterotome 350 having guidewire 352 being successfully inserted into the major papilla opening 310 and within bile duct 314. Here, the MR-ERCP system of disclosure described herein is configured such that the real-time images or video streams of FIGS. 4A and 4B are made available to the user of device 200, wherein the user has the ability to view the foregoing images or videos in real time along with holographic images 250A.

Figure 5A:
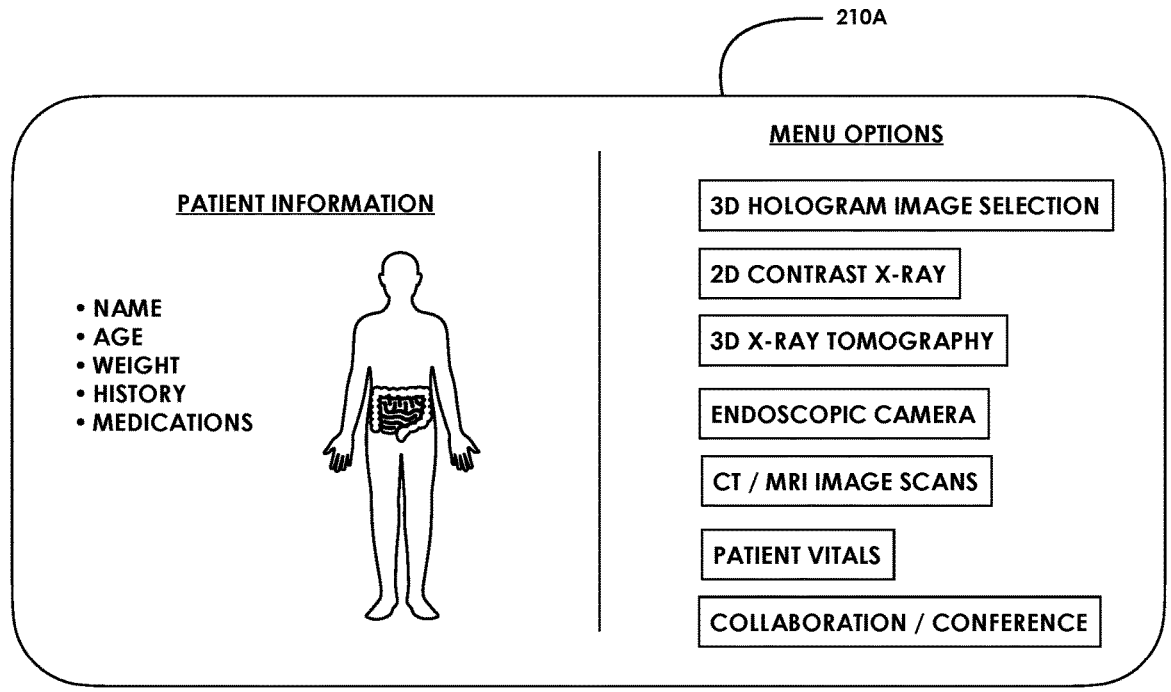
FIG. 5A illustrates a graphical screen, projection, or holographic visualization portal of the MR-ERCP system, method, and apparatus of the disclosure described herein, depicting in one non-limiting exemplary embodiment various patient information and menu options.
Figure 5B:
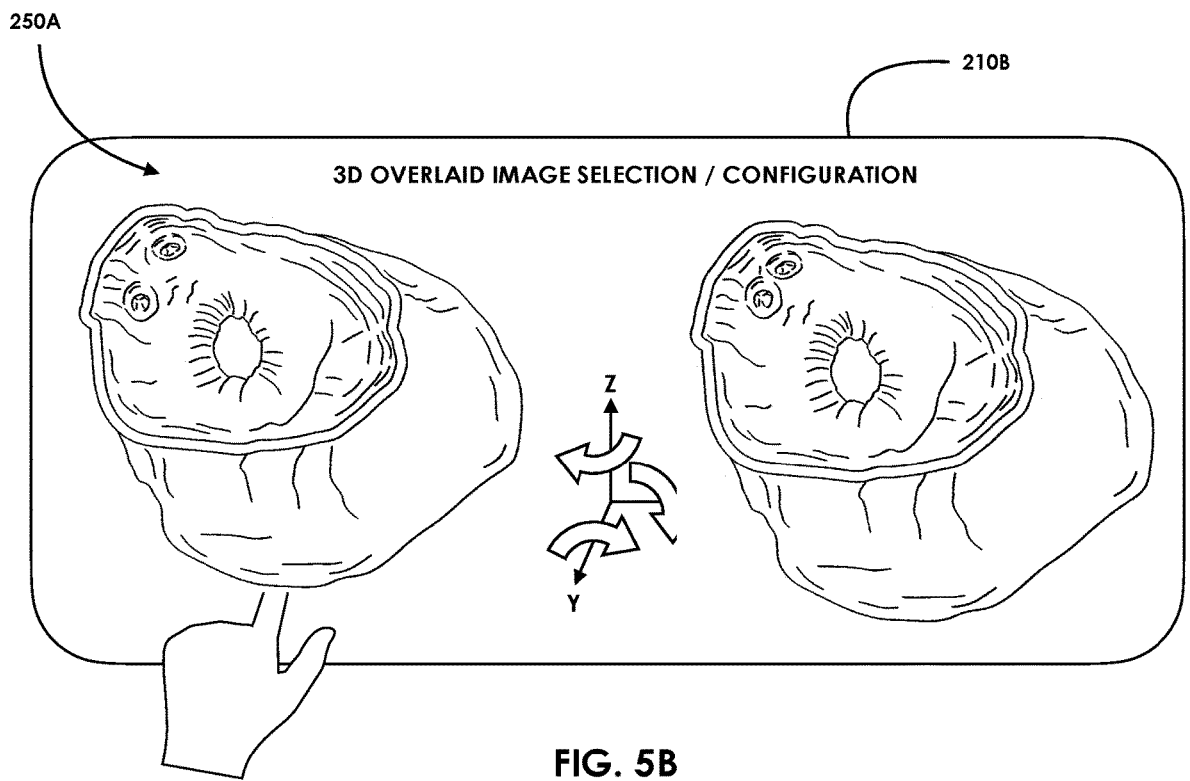
FIG. 5B illustrates another graphical screen, projection, or holographic visualization portal of the MR-ERCP system, method, and apparatus of the disclosure described herein, depicting various views of the three-dimensional cranial part of the duodenum.

FIG. 5A illustrates one non-limiting exemplary embodiment of a main portal display 210A for the HMD of device 200. In particular, portal display 210A may display to the user's HMD various information and options pertaining to an ERCP procedure. In particular, this may include various patient information retrieved, downloaded, or transmitted to device 200, such as name, age, weight, medical history, and current medications. This may also include patient data that is relevant or specific to a particular ERCP procedure. In addition, portal 210A can provide multiple menu options for the user or physician. Here, depending on the ERCP being performed, the user can select the specific three-dimensional holographic image 250A of the duodenum to be displayed to the user on the HMD of device 200. For example, once the menu option pertaining to the 3D hologram image is selected, the user may be directed to portal 210B shown in FIG. 5B. As shown in FIG. 5B, the user can scroll or browse through various variations of the duodenum and major papilla depending on the patient, as the major papilla anatomy can vary from patient to another patient. Once the appropriate holographic image 250A of the duodenum is selected, then the HMD of device 200 will display that holographic image during the ERCP. In addition, the physician or user may also have the option to select the appropriate holographic image 250A during the ERCP, or at the time the physician is able to view the endoscopic camera video to determine the appropriate image 250A of the duodenum depending on that particular patient's anatomy. In addition, the user may also manipulate and calibrate any of images 250A relative to the patient on the operating table at this stage.

Figure 6:
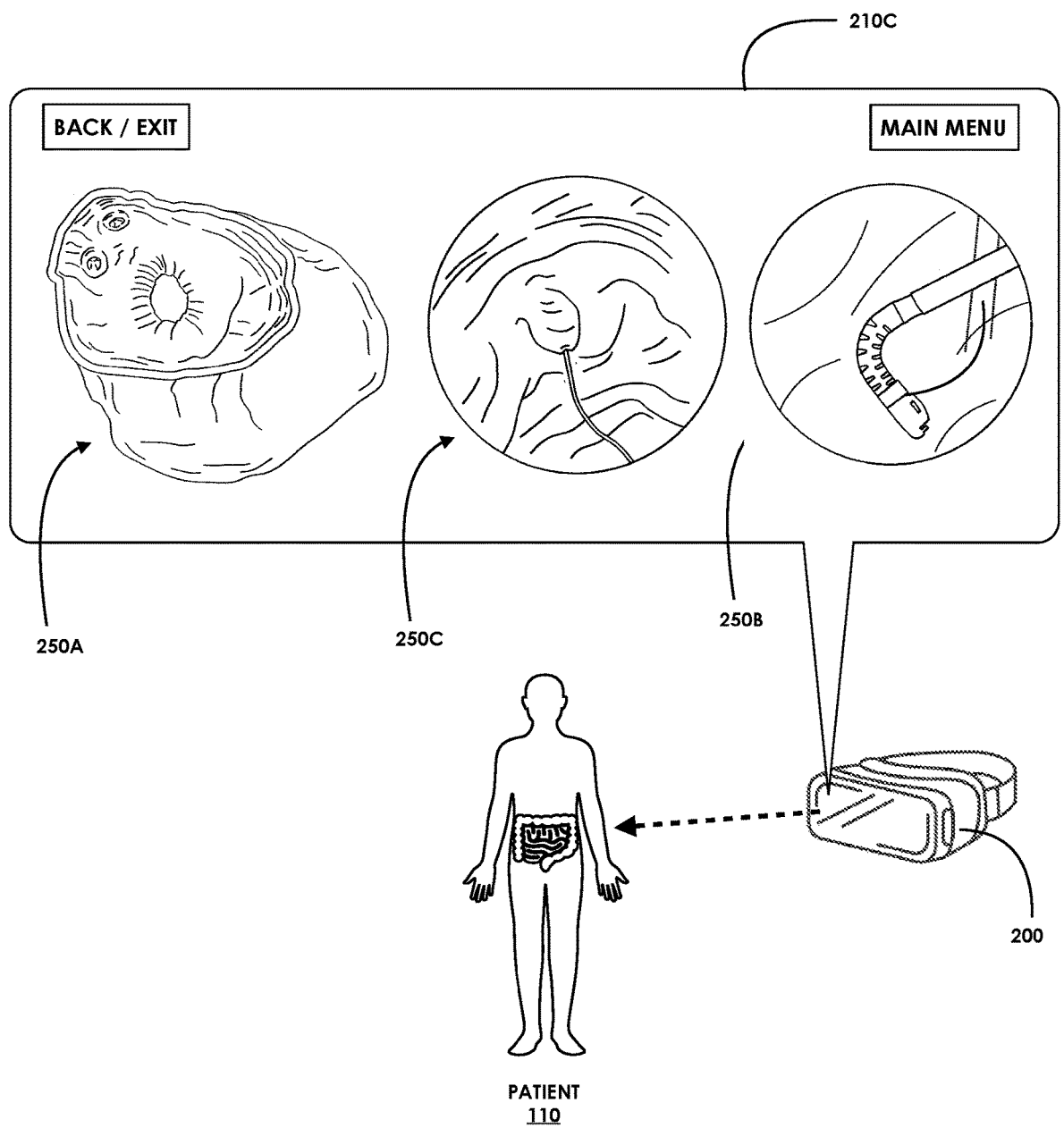
FIG. 6 illustrates another graphical screen, projection, or holographic visualization portal of the MR-ERCP system, method, and apparatus of the disclosure described herein and a simplified top view of a patient and a simplified perspective view of a headset of the MR-ERCP, further depicting various three-dimensional, endoscopic, and x-ray views shown in relation to each other during an ERCP procedure of the patient in real-time.

Referring back to FIG. 5A, the user may also have the option to select various other images or video. For example, the user may also select one or more 2D contrast x-ray images or video sources or 3D MRCP or CT abdomen reconstructions of the cranial views of the duodenum, in addition to the endoscopic camera video feed to be shown on the HMD device 200 in conjunction with holographic image 250A. For example, once 2D contrast x-ray images and the endoscopic camera video feed menu options are selected, the user may be directed to portal 210C shown in FIG. 6. Here, as shown in FIG. 6, the user can view image 250A, image/video 250B, and image/video 250C directly next to each other or juxtaposed relative to each other, simultaneously and in real-time, on the HMD of device 200 while performing the ERCP procedure on patient 110 on the operating table. In particular, the user may also have the option to adjust any of the positions of items 250A, 250B, and 250C relative to each other, such as moving them to the sides, above, below, zooming in/out, or minimizing the items from view. In addition, the user may also have the ability to calibrate, "lock in", or center any of images 250A, 250B, and 250C relative to each other. Further, the user can also predefine the transparency or opacity of any of items 250A, 250B, and 250C such that it does not interfere with the physician's field of view of his or her physical environment.

It is important to note that in conventional ERCP procedures, the surgeon is required to periodically view different monitors of the x-ray video and also the endoscopic video, and periodically moving back and forth between each monitor to gauge or "get a feel" for where the guidewire is within the duodenum relative to the major papilla, which can result in unsuccessful cannulation of the major papilla orifice. This is partly due to the fact that the physician does not have all of the information pertaining to the location of the guidewire available to it at any given instant in time, thus requiring the physician periodically view various monitors (such as one monitor at a time) and make predictions of where the position of sphincterotome and guidewire are relative to the patient's major papilla. However, as shown in FIG. 6 of the disclosure described herein, by having effectively all three items 250A, 250B, and 250C juxtaposed next to each other and available to the surgeon's direct field of view, in real time and as the surgeon is working on the patient, the surgeon is able predict and calculate with much higher accuracy the exact position of the sphincterotome and guidewire relative to the patient's major papilla in order to achieve successful cannulation.

Figure 7A:
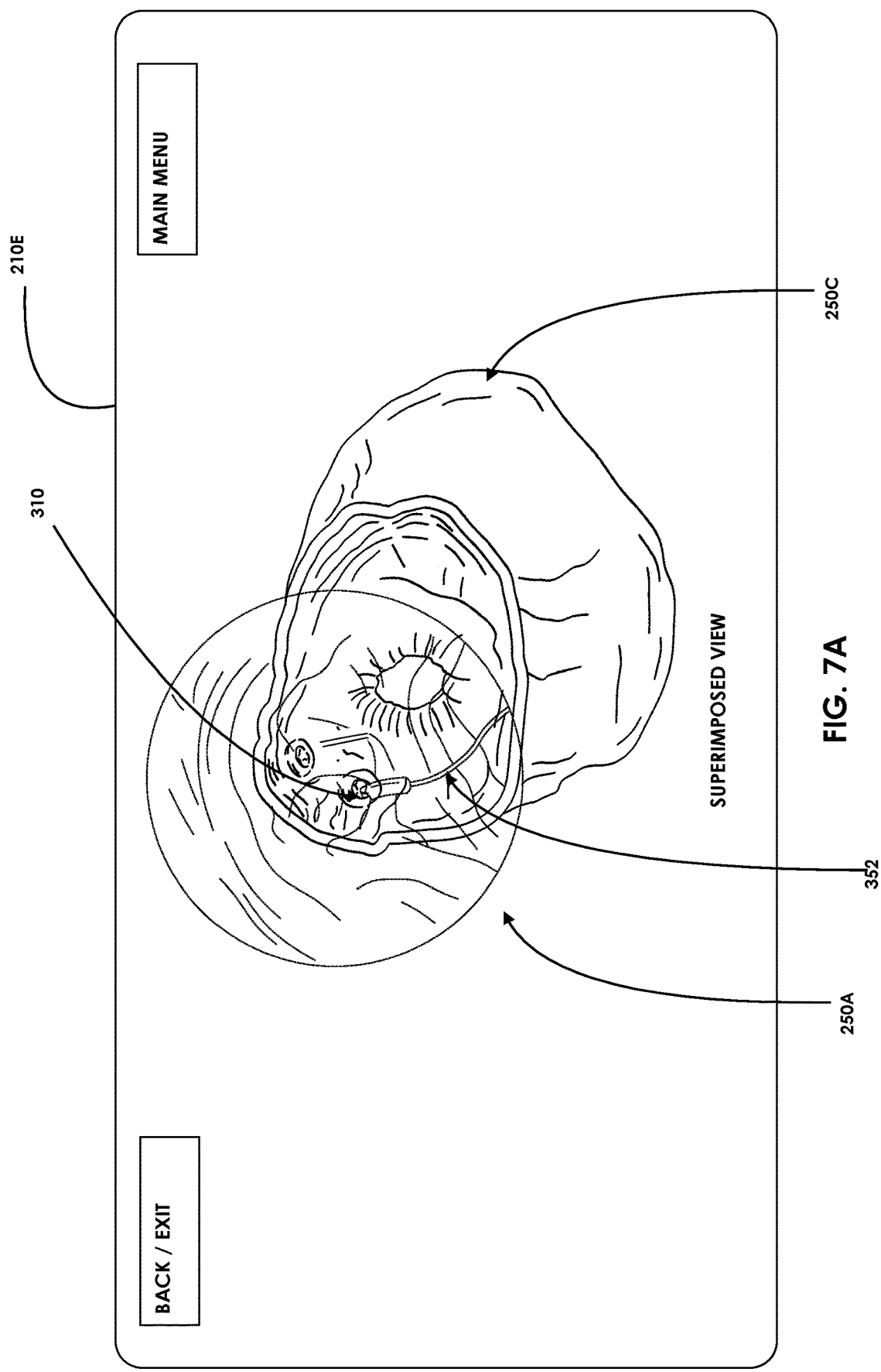
FIG. 7A illustrates another graphical screen, projection, or holographic visualization portal of the MR-ERCP system, method, and apparatus of the disclosure described herein, depicting a three-dimensional view of the duodenum superimposed or juxtaposed on an endoscopic internal camera view of the duodenum in real-time.
Figure 7B:
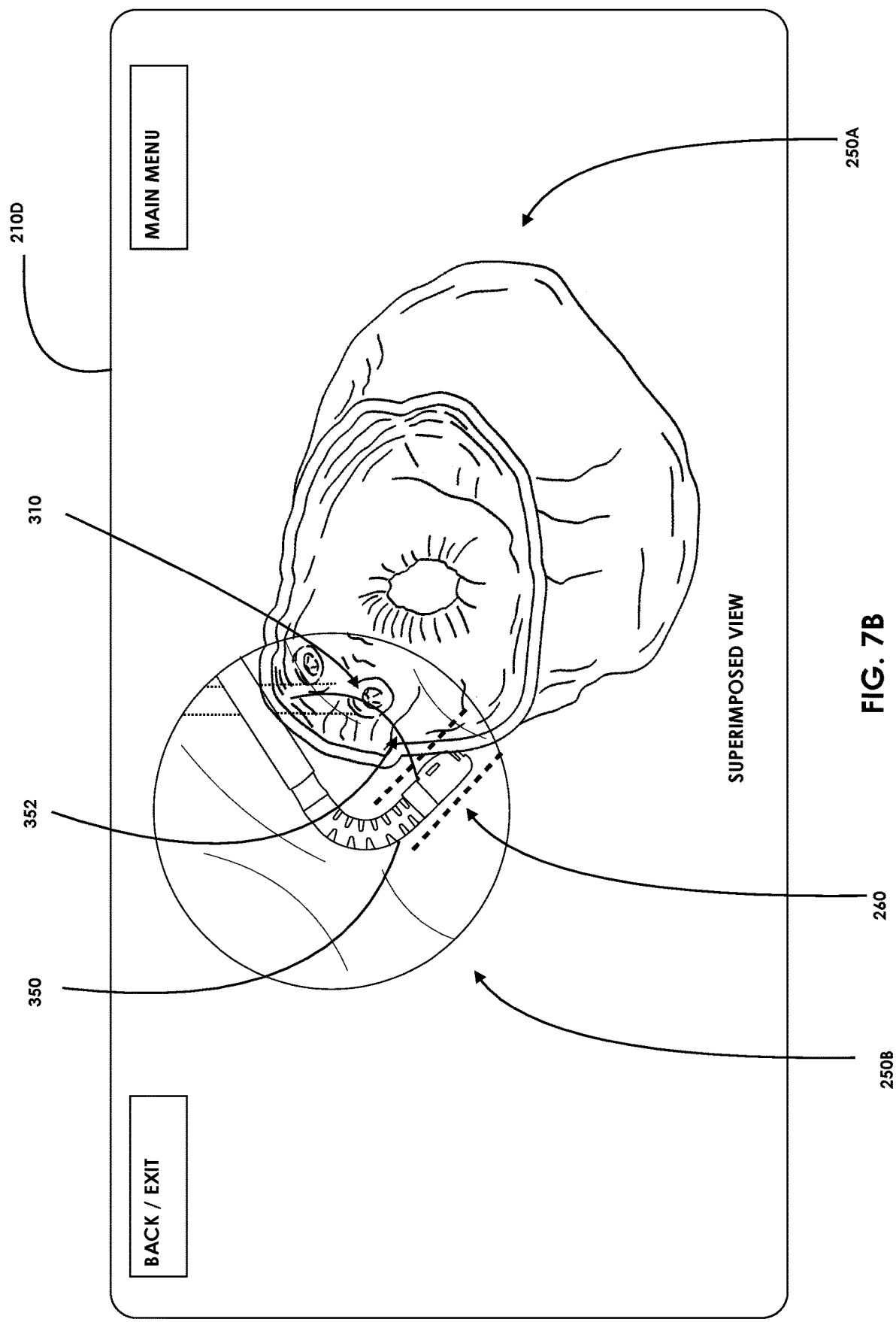
FIG. 7B illustrates another graphical screen, projection, or holographic visualization portal of the MR-ERCP system, method, and apparatus of the disclosure described herein, depicting a three-dimensional view of the duodenum superimposed or juxtaposed on an x-ray view of the duodenum in real-time.

Referring back to FIG. 5A, the surgeon may also have the option to superimpose or directly overlay one image on top of another image or video. For example, as shown in FIG. 7A, holographic image 250A may also be juxtaposed, overlaid or superimposed directly or at least partially on top of the endoscopic video camera feed 250C (or vice versa), such that the surgeon is able to view the endoscopic camera video directly through the holographic image 250A to further assist in accurate cannulation of the major papilla. Here, as shown, the position and orientation of video or image feed 250C may be such that the major papilla orifices 310 on each image are approximately axially aligned with each other to provide a more realistic perception of the location of the sphincterotome and/or guidewire relative to the orifice 310. In addition, as shown in FIG. 7B, holographic image 250A may also be juxtaposed, overlaid or superimposed directly or at least partially on top of the x-ray video feed 250B, such that the surgeon is able to view the x-ray video directly through the holographic image 250A to further assist in accurate cannulation of the major papilla. Here, as shown, the position and orientation of video or image feed 250B may be such that the major papilla orifices 310 on each image are approximately axially aligned with each other to provide a more realistic perception of the location of the sphincterotome and/or guidewire relative to the orifice 310. In addition, the HMD of device 200 may also display guided lane markers or guided visual representations 260 that are in about 10 to 11 o'clock positions that can assist the surgeon in aligning the sphincterotome 350 in a specific position or orientation relative to the ampulla opening 310 in order to achieve successful cannulation of the major papilla via guidewire 352. In addition, through image recognition, device 200 can also alert and notify the surgeon on the HMD when he or she has successfully positioned sphincterotome 350 within guided lanes of the visual representation 350. Here, the foregoing visual representation 210 may also be used in conjunction with any other image or video, such as the endoscopic camera image or video or a 3d reconstructed MRCP/CT image of the cranial part of the duodenum in the region of the major papilla. In addition, similar guided visual representations may also be used—with respect to the position and orientation of the guidewire. Here, it is contemplated within the scope of the present disclosure described herein that any type of image or video data may interchanged and super imposed or overlaid on top of each other. In addition, device 200 may also automatically (or manually) adjust opacity levels of each of items 250A, 250B, and 250C relative to each other, wherein one item may be more opaque or transparent relative to another item.

Figure 8:
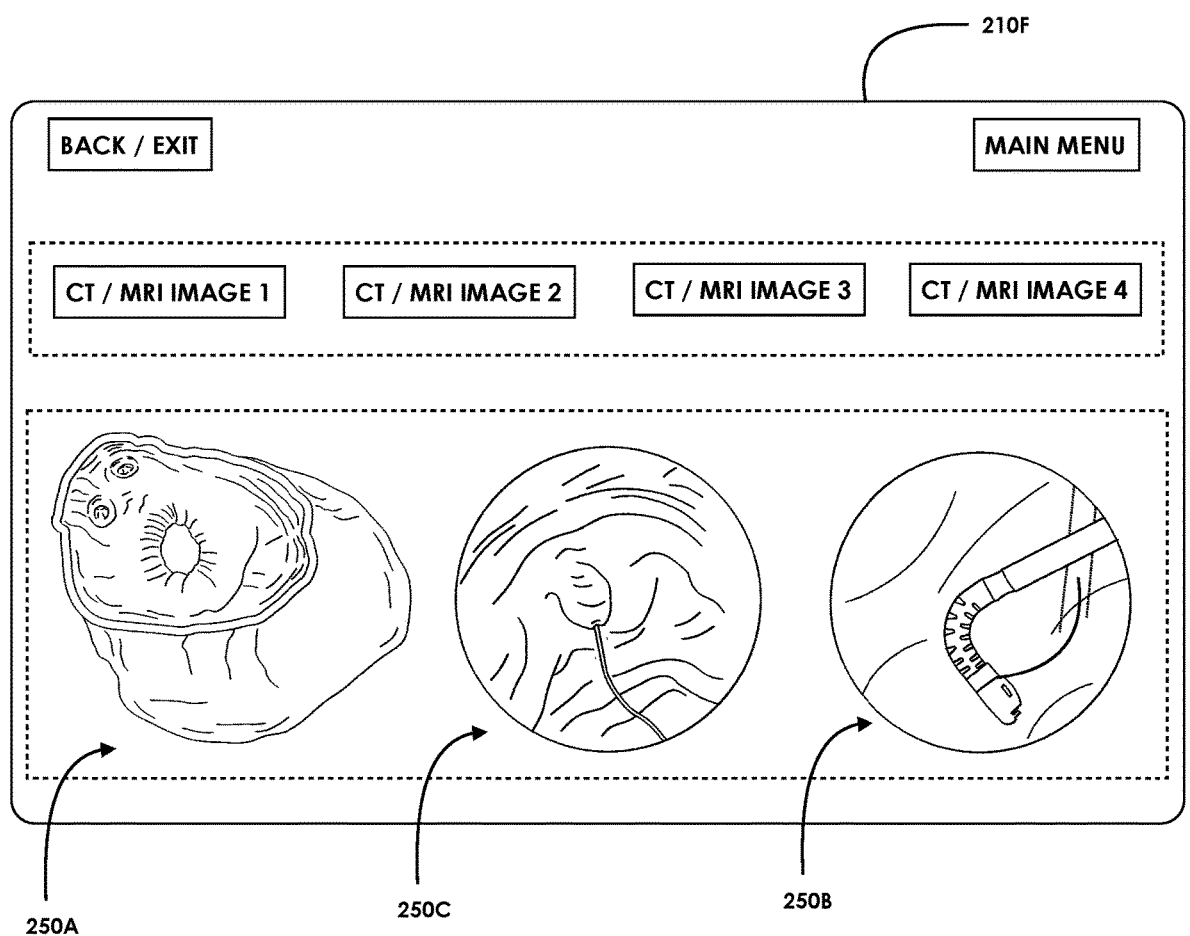
FIG. 8 illustrates another graphical screen, projection, or holographic visualization portal of the MR-ERCP system, method, and apparatus of the disclosure described herein, depicting various three-dimensional, endoscopic, and x-ray views shown in relation to each other during an ERCP procedure of the patient in real-time in conjunction with CT and/or MRI image scans.

Referring back to FIG. 5A, the surgeon may also be able to select and view various CT, MRI, or MRCP scan images to be displayed on the HMD of device 200 in conjunction with one or more of images or videos 250A, 250B, and/or 250C. For example, once the CT/MRI image scans menu icon or option is selected by the user, the HMD of device 200 can direct the user to portal 210F of FIG. 8. Here, the operating surgeon may be able to view multiple CT and/or MRI/MRCP scan images next to each and further juxtaposed relative to items 250A, 250B, and 250C. In particular, the CT and/or MRI/MRCP images, particularly the coronal views, can further assist the surgeon in case of complicated anatomy such as congenital anomalies of the ducts, pancreatic tumors and bile duct tumors. In addition, as shown in FIG. 11, the user can also elect to show holographic images 250A, 250B, and 250C in conjunction with three dimensional holographic image 250D illustrating an MRCP reconstruction of the patient's duodenum, bile duct, and ampulla, among others.

Figure 9:
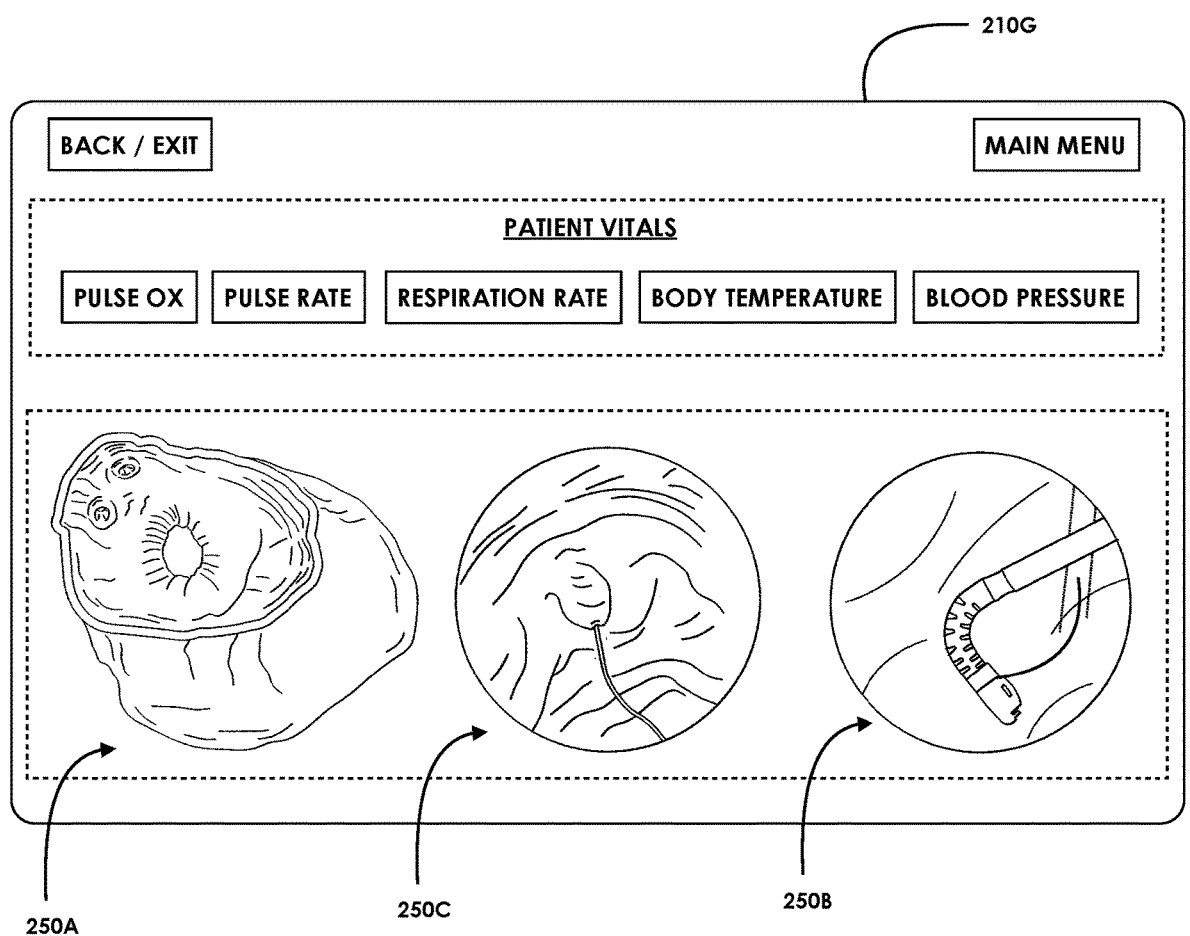
FIG. 9 illustrates another graphical screen, projection, or holographic visualization portal of the MR-ERCP system, method, and apparatus of the disclosure described herein, depicting various three-dimensional, endoscopic, and x-ray views shown in relation to each other during an ERCP procedure of the patient in real-time in conjunction with various patient vitals information.

Referring back to FIG. 5A, the surgeon may also be able to select and view various patient vital data information in real-time to be displayed on the HMD of device 200 in conjunction with one or more of images or videos 250A, 250B, and/or 250C. For example, once the patient vitals menu icon or option is selected by the user, the HMD of device 200 can direct the user to portal 210G of FIG. 9. Here, the operating surgeon may be able to view various patient vital information that can be directly transmitted over a network to device 200 in real time, and further juxtaposed relative to items 250A, 250B, and 250C. For example, such patient vital information can be real time patient electrocardiogram (ECG) data, pulse oximeter, pulse rate, respiration rate, body temperature, and blood pressure, among others. In particular, by having direct access to the forgoing data in real time, the surgeon is able to instantly view patient vitals during a procedure as opposed to relying on external monitors or operating room personnel for such data.

Figure 10:
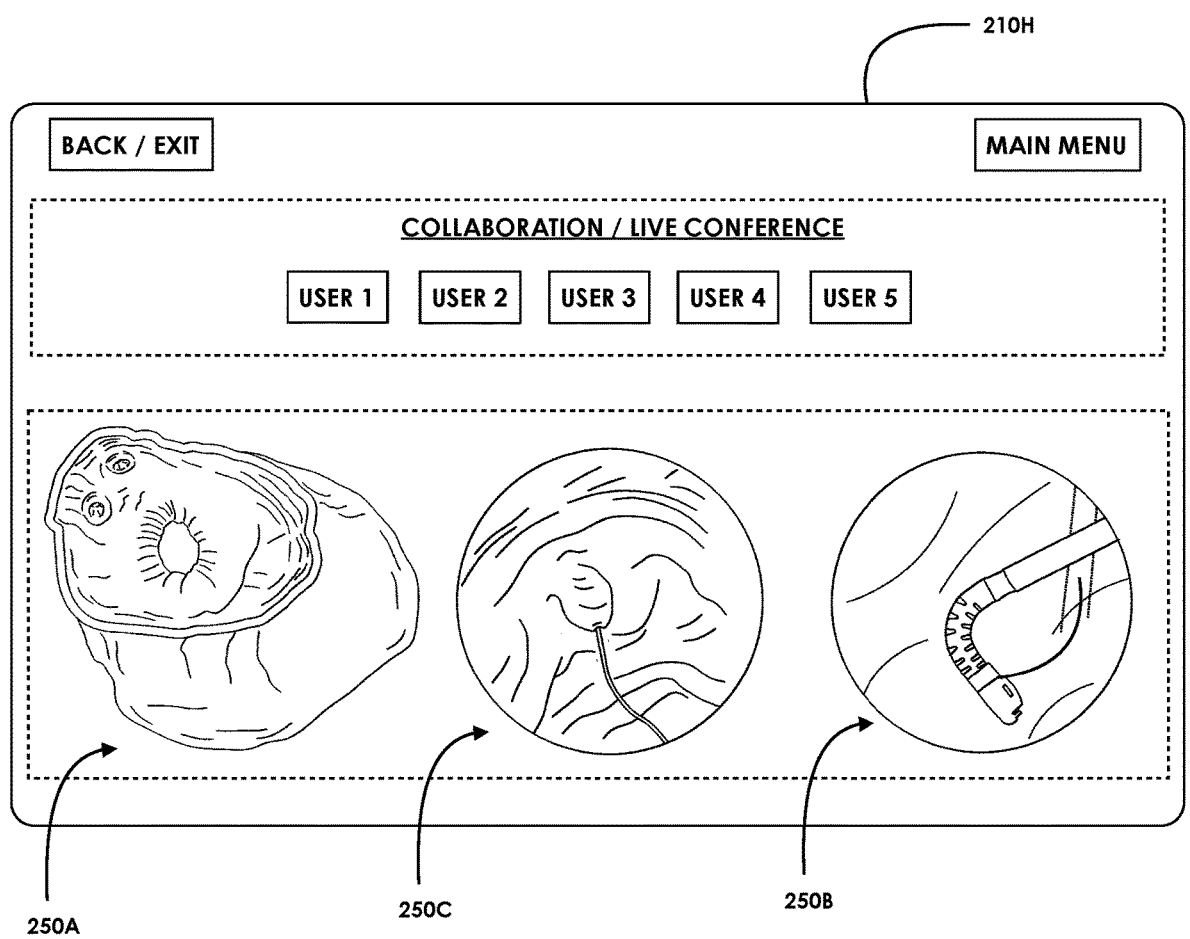
FIG. 10 illustrates another graphical screen, projection, or holographic visualization portal of the MR-ERCP system, method, and apparatus of the disclosure described herein, depicting various three-dimensional, endoscopic, and x-ray views shown in relation to each other during an ERCP procedure of the patient in real-time in conjunction with live collaboration and/or conferencing of various users.

Referring back to FIG. 5A, the surgeon may also be able to select, view, share, and/or collaborate or conference in with multiple other users of the MR-ERCP network of the disclosure described herein. For example, once the collaboration/conference menu icon or option is selected by the user, the HMD of device 200 can direct the user to portal 210H of FIG. 10. In particular, the surgeon may have the option to share his or her screen or visual representation on the HMD of device 200 with any number of authorized users during an ERCP. In addition, the surgeon may also have the ability to orally and visually communicate and chat with the various users via device 200. As an example, the surgeon may be able to collaborate and/or provide instructional training material during a live ERCP procedure on a patient. Further, any of users 1-5 may also have their own respective HMD's that can communicate over the network with the HMD of device 200, wherein each user 1-5 can view the same visual representation depicted on the HMD of device 200 of the operating physician. In addition, the user of device 200 may also have the ability to share certain information (such as images 250A, 250B, and 250C), but not share other information (such as patient information or patient vitals).

As discussed with any of the embodiments with respect to FIGS. 5A-11, the user of device 200 has the ability to save various user profiles or patient profiles, or procedure templates. As an example, for a particular ERCP surgery, the physician or user may have to create custom templates for the HMD of device 200, wherein those templates include any of items 250A-250D, at any configuration or orientation relative to each other. As a further example, the user may want to save the profile or template depicted in the portal of 210C of FIG. 6, wherein the positions, configurations, and properties of the various items 250A-250D are saved to be reused for another ERCP procedure. Alternatively, the user may be able to recall multiple different profiles or templates, and further switch between them during a procedure.

Further, the HMD of device 200 may also be configured to create a virtual reality endoscopy lab. For example, the endoscopy lab can be configured as a virtual room that can allow the user of the device 200 to interact with various forms of data, people, images, or video, For example, the user may be able to view radiology reports and other patient information in real time. In addition, other users (having their own computing device or device 200) may also enter the virtual endoscopy lab and communicate with each other via their respective devices 200. As an example, the ERCP surgeon may have a virtual conversation with a radiologist regarding certain findings or anomalies in a patient's scans.

In addition, it is contemplated within the scope of the present disclosure described herein that in lieu of the HMD of mixed reality device 200, MR-ERCP system may also allow the surgeon to generate and project a holographic screen that is commensurate with the portals as discussed with respect to FIGS. 5A-10. In addition, such a generated holographic screen may also be shared and viewed by multiple other users of the MR-ERCP system of the disclosure described herein, such as described with respect to the embodiment of FIG. 10.

In addition, it is contemplated within the scope of the present disclosure described herein that the methods and systems disclosed herein may be used with respect to any medical or dental related procedures. As an example, the device 200 may also be used by a dentist, endodontist, periodontist, or surgeon to provide a holographic images of the mouth, teeth, or root canals for examination and operating purposes. Similarly, the disclosed systems and processes may also be used by other physicians and medical professionals, such as cardiologists with respect to heart surgery or neurosurgeons with respect to brain surgery, among others. In another example, an orthopedic surgeon may be able to virtually view cracked or fractured bones, vertebrae, or ligaments in a holographic representation to assist with surgery. From the foregoing it will be seen that the present disclosure described herein is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts described herein, except insofar as such limitations are included in following claims. Further, it will be understood that certain features and sub-combinations are of utility and may be employed without reference to other features and sub-combinations. This is contemplated by and is within the scope of the claims.

What is claimed is:

1. A mixed reality endoscopic surgical procedure method, comprising:
 selecting a three-dimensional holographic first image comprised of a duodenum and ampulla representative of a patient's duodenum and ampulla from a plurality of three-dimensional holographic images representative of the patient's duodenum and ampulla, wherein the three-dimensional holographic first image of the duodenum graphically displays the ampulla at a head mounted display;
 superimposing the three-dimensional holographic first image over a video of the patient's duodenum;
 positioning a sphincterotome relative to the patient's duodenum, wherein the sphincterotome further comprises a guidewire;
 displaying one or more graphical markers at least partially disposed on the three-dimensional holographic first image, wherein the one or more graphical markers are adjacent to the graphically displayed ampulla;
 aligning, axially, a distal end of the sphincterotome with the one or more graphical markers; and
 penetrating the patient's ampulla via the guidewire of the sphincterotome using the graphical markers on the three-dimensional holographic first image as a visual guide.

2. The mixed reality endoscopic surgical procedure method of claim 1, wherein the one or more graphical markers are comprised of lane markers.

3. The mixed reality endoscopic surgical procedure method of claim 1, wherein the one or more graphical markers are at about 10 o'clock position relative to the vertical plane from the viewpoint on the head mounted display.

4. A mixed reality endoscopic surgical procedure method, comprising:
 selecting a three-dimensional holographic first image of a duodenum representative of a patient's duodenum via a head mounted display from a plurality of three-dimensional holographic images representative of the patient's duodenum, wherein the three-dimensional holographic first image of the duodenum graphically displays an ampulla;
 displaying the three-dimensional holographic first image adjacent to a video of the patient's duodenum on the head mounted display;
 positioning a sphincterotome relative to the patient's duodenum, wherein the sphincterotome further comprises a guidewire;

displaying one or more graphical markers at least partially disposed on the three-dimensional holographic first image on the head mounted display, wherein the graphical markers are adjacent to the graphically displayed ampulla;

aligning, axially, a distal end of the sphincterotome with the one or more graphical markers via the head mounted display; and penetrating the patient's ampulla via the guidewire of the sphincterotome using the graphical markers on the three-dimensional holographic first image as a visual guide.

\* \* \* \* \*